United States Patent
Sokolov et al.

(10) Patent No.: US 10,667,728 B2
(45) Date of Patent: Jun. 2, 2020

(54) METHOD FOR DETERMINING GLUCOSE CONCENTRATION IN HUMAN BLOOD

(71) Applicant: Healbe Corporation, Redwood City, CA (US)

(72) Inventors: Evgeniy L. Sokolov, Gatchina (RU); Andrey A. Chechik, St. Petersburg (RU); Vladimir Y. Elokhovskiy, St. Petersburg (RU)

(73) Assignee: Healbe Corporation, Redwood City, CA (US)

( * ) Notice: Subject to any disclaimer, the term of this patent is extended or adjusted under 35 U.S.C. 154(b) by 4 days.

(21) Appl. No.: 15/787,432

(22) Filed: Oct. 18, 2017

(65) Prior Publication Data

US 2018/0035930 A1 Feb. 8, 2018

Related U.S. Application Data

(63) Continuation of application No. 14/466,570, filed on Aug. 22, 2014, which is a continuation of application No. PCT/RU2013/000144, filed on Feb. 22, 2013.

(30) Foreign Application Priority Data

Feb. 24, 2012 (RU) ................. 2012106461

(51) Int. Cl.
*A61B 5/053* (2006.01)
*G01N 27/02* (2006.01)
*A61B 5/145* (2006.01)

(52) U.S. Cl.
CPC .......... *A61B 5/14532* (2013.01); *A61B 5/053* (2013.01); *G01N 27/02* (2013.01)

(58) Field of Classification Search
CPC ..... A61B 5/14532; A61B 5/053; G01N 27/02
See application file for complete search history.

(56) References Cited

U.S. PATENT DOCUMENTS

| 5,792,668 A | 8/1998 | Fuller |
|---|---|---|
| 6,517,482 B1 | 2/2003 | Elden |

(Continued)

FOREIGN PATENT DOCUMENTS

| JP | 2009005842 A | 1/2009 |
|---|---|---|
| JP | 2011078443 A | 4/2011 |

(Continued)

OTHER PUBLICATIONS

International Search Report from International Application No. PCT/RU2013/000144, filed Feb. 22, 2013, dated Jul. 11, 2013.

(Continued)

*Primary Examiner* — Jacqueline Cheng
*Assistant Examiner* — Tho Q Tran
(74) *Attorney, Agent, or Firm* — Patentbar International, P.C.

(57) ABSTRACT

Measuring the impedance of a human body region at a high frequency ($Z_{HF}$) and a low frequency ($Z_{LF}$). $Z_{HF}$ is used to obtain the value of the volume of fluid in the tissues of the region. $Z_{LF}$ is used to obtain the value of the volume of extracellular fluid in the tissues. The increase in the metabolic component in the volume of extracellular fluid is determined by the increase of the volume of all of the fluid in comparison with the previous measurement, determining the increase in the volume of extracellular fluid in comparison with the previous measurement and subsequently calculating the difference between the increases in the volume of all of the fluid and the volume of extracellular fluid. The glucose concentration $G(t_k)$ is determined by adding the amount of increase in the glucose concentration and the value of the glucose concentration determined at the previous measuring stage.

5 Claims, 3 Drawing Sheets

(56) References Cited

U.S. PATENT DOCUMENTS

| | | |
|---|---|---|
| 6,841,389 B2 | 1/2005 | Novikov |
| 7,050,847 B2 | 5/2006 | Ollmar |
| 2010/0130883 A1 | 5/2010 | Carpenter et al. |
| 2011/0224521 A1 | 9/2011 | Gericke et al. |

FOREIGN PATENT DOCUMENTS

| | | |
|---|---|---|
| RU | 2073242 C1 | 2/1997 |
| RU | 2088927 C1 | 8/1997 |
| RU | 9703 U1 | 5/1999 |
| RU | 2342071 C2 | 12/2008 |
| WO | 00/09996 A1 | 2/2000 |
| WO | 2009/033625 A1 | 3/2009 |
| WO | 2010/126827 A2 | 11/2010 |

OTHER PUBLICATIONS

Lindholm-Sethson Britta et al., Multivariate analysis of skin impedance date in long-term type 1 diabetic patients, Chemometrics and Intelligent Laboratory Systems, Dec. 14, 1998, pp. 381-394, vol. 44, issues 1-2.

Turapov, U. U., Assessment of glycemia by skin impedance in acupoints using blood glucose level identification models: diabetes mellitus case study, 1991, Author's Abstract of Ph.D dissertation, Tashkent.

METHOD FOR DETERMINING GLUCOSE CONCENTRATION IN HUMAN BLOOD

RELATED APPLICATIONS

This Application is a Continuation Application of U.S. nonprovisional application Ser. No. 14/466,570 filed on Aug. 22, 2014, which in turn is a Continuation Application of International Application PCT/RU2013/000144, filed on Feb. 22, 2013, which in turn claims priority to Russian Patent Applications No. RU2012106461, filed Feb. 24, 2012, all of which are incorporated herein by reference in their entirety.

FIELD OF THE INVENTION

The invention refers to non-surgical methods for medical examination of human health, namely, to methods for determining glucose concentration in human blood as a result of measuring the impedance of human body part.

BACKGROUND OF THE INVENTION

Non-invasive methods for determining glucose concentration in human blood based on measuring the electrical impedance of a human body part or impedance components are known.

For example, a method for the indication of sugar content in human blood is known [RU Pat. No. 2073242, G01N33/4, 1997], with which sugar content level is determined based on variation of dielectric permeability of a finger placed in the electrical field of transducer.

A method for monitoring the amount of sugar in human blood is also known [RU Pat. No. 2088927, G01N33/49, 1997], with which the measurement is taken by changing the reactance of oscillating circuits included in the secondary circuits of high-frequency generator via direct action of human upon oscillating circuits elements. With this method, the amount of sugar in blood is determined based on variation of current in the secondary circuits of high-frequency generator.

Another method is known [U.S. Pat. No. 5,792,668, G01N27/00, 1998], with which spectral analysis of high-frequency radiation reflected by human body or passing through the human body is conducted. The phase shift between direct and reflected (or transmitted) waves, which characterizes the reactive component of electrical impedance, represents a parameter to be measured by this method. The concentration of substances contained in the blood (in particular, glucose concentration) is determined based on measured parameters of phase spectrum.

Another method is known, which was embodied in a device described in the RU Pat. No. 9703U1, A61B5/00, 1999. Glucose concentration is determined by this device based on measurement of human body region impedance at two frequencies, determining capacitive component of impedance and converting the obtained value of capacitive component into glucose concentration in patient's blood.

A method for measuring glucose concentration in human blood non-invasively is known [U.S. Pat. No. 6,517,482, A61B5/00, 2003]. The method is based on measuring impedance between two electrodes at a number of frequencies and deriving the value of glucose concentration on the basis of measured values.

Another method for determining glucose concentration in blood non-invasively is known, which involves measuring electric transfer functions by means of two pairs of four-electrode sensors [RU Pat. No. 2342071, A61B5/053, 2008]. The concentration of glucose in blood is determined based mathematical model specified in advance.

Another method for determining glucose concentration in human blood is also known [U.S. Pat. No. 7,050,847, A61B5/00, 2006], with which impedance of a human body area is measured at different frequencies by means of sensors. Impedance value at high frequencies is related to fluid volume in body tissues, while impedance value at low frequencies—to volume of extracellular fluid. Parameters of biological fluids in the human body are determined based on the measured values, and then glucose concentration in human blood is derived from these parameters.

However, the above-described methods are characterized by one common disadvantage—namely, the values of glucose concentration in human blood obtained through the use of these methods rank below the values obtained using direct invasive methods in terms of measurement accuracy. At the same time, invasive methods, which require taking samples of blood, rank below non-invasive ones in terms of convenience and safety.

An engineering problem to be solved by the present invention consists in working out a non-invasive method for continuous determination of glucose concentration in human blood that is characterized by higher accuracy as compared to currently known non-invasive methods.

SUMMARY OF THE INVENTION

A method of measuring of a concentration of blood glucose in a human, the method comprising:

using spaced apart electrodes attached to a region of a body of the human to successively measure values of high frequency impedance and low frequency impedance of the region at predetermined time intervals;

using a measured value of the high frequency impedance to determine an estimate of a volume of fluid in tissue of the region between the electrodes;

using a measured value of the low frequency impedance to determine an estimate of a volume of an extracellular fluid in the tissue in the region between the electrodes;

determining an increment of a metabolic component of the volume of the extracellular fluid by:

determining an increment of the estimate of the volume of the fluid relative to a previously measured value of the volume of the fluid;

determining an increment of the estimate of the volume of the extracellular fluid relative to a previously measured value of the volume of the extracellular fluid;

determining a difference between the increment of the estimate of the volume of the fluid and the increment of the estimate of the volume of the extracellular fluid;

determining an increment of the concentration of the blood glucose by normalizing the increment of the metabolic component of the volume of the extracellular fluid; and determining the concentration of the blood glucose by adding up the increment of the concentration of the blood glucose and a previously determined concentration of the blood;

wherein determining a concentration of the blood glucose at a first time interval comprises adding up an increment of the concentration at the first interval of time and an initial blood glucose concentration.

The principal physics of the method consists in measuring the volume of fluid in a human body region. The water in human body accounts for 70% of body weight, and it is not present in the human body as a single space, but distributed among body tissues. Vascular walls and cell membranes (out of which consist all tissues of human body) serve as boundaries for fluids. It is generally accepted to distinguish three water spaces: intracellular fluid, intravascular fluid (blood plasma fluid) and intercellular fluid (fluid that fills the intercellular space).

The intracellular fluid or fluid contained within tissue cells and red blood cells accounts for approximately 30-40% of human body weight.

Intravascular fluid and intercellular fluid form the space of extracellular fluid, which accounts for about 20% of human body weight.

Substances intended for sustaining the life of cells or products of their vital activity that are to be disposed of or reprocessed inside human body are present in each type of fluid. These substances move through cell membranes from one space to another in the process of vital activity of the human body. Osmotic pressure that depends upon difference in concentration (concentration gradient) of substances on different sides of the membrane represents one of the driving forces for this motion.

A dynamic equilibrium of metabolic processes is observed in the state of rest. The appearance of concentration gradient of osmotic pressure (e.g., together with glucose inflow from gastrointestinal tract after food intake) forces water to move though cell membrane in the direction of space characterized by higher concentration of solids dissolved in it. The volumes of water sectors are changed as a result of this process. But then regulatory mechanisms striving to restore the disturbed equilibrium of these spaces come into action. In other words, changes of water spaces volumes of human body have characteristic (cyclic) specific features. These specific features can be used as indicators of the character of metabolic processes in the human body, e.g. increase of glucose concentration in human blood after food intake.

The basis of the method consists in estimating an increase or decrease of glucose concentration in the blood based on changes of water spaces in the human body in time, which is determined in the course of periodic measurements of impedance of a human body region.

The following steps are performed in particular embodiments of the method.

Initial value of glucose concentration in human blood is determined in the beginning of measurements (using an alternative method—either invasive or non-invasive one). This absolute value is individual for every human being and it determines not only the nature of dynamics of glucose concentration changes, but also its absolute values during different periods of life activity of human being.

In particular, at least two electrodes installed at a certain distance from one another (preferably on peripheral body regions—e.g. a finger or an arm) can be used for measuring the impedance of a human body region.

Measurements of impedance of a human body region at high and low frequencies are taken with a predetermined time interval from 1 sec to 10 min. For the sake of convenience of hardware implementation of the method these time interval should be equal.

The moment of food intake is recorded during measurement taking, and this fact is used to adjust the indicators of dynamics of glucose supply into the human body.

Specifically, the following parameters are determined when implementing the method based on values of human body region impedance measured at high and low frequencies at points in time $t_k$:

1) Volume of fluid contained in the tissues of the human body region between electrodes $W_{sum}(t_k)$ is calculated from the equation:

$$W_{sum}(t_k)=A \cdot L^2/Z_{HF}(t_k),$$

where: L—the distance between two electrodes;
$Z_{HF}(t_k)$ is the high frequency HF impedance measured at time $t_k$;
A is a calibration factor determined as:

$$A=V_{sum} \cdot Z_{HF}/L^2,$$

where: $V_{sum}$ is a preliminary determined value of the volume of fluid in the tissue in the region between the electrodes;
$Z_{HF}$—preliminary determined high frequency HF impedance;

2) $W_{out}(t_k)$ is the volume of the extracellular fluid in the tissue of the region between the electrodes determined according to the following equation:

$$W_{out}(t_k)=B \cdot L^2/Z_{LF}(t_k),$$

where: $Z_{LF}(t_k)$ is the low frequency LF impedance measured at time $t_k$;
B is a calibration factor, calculated as:

$$B=V_{out} \cdot Z_{LF}/L^2;$$

where: $V_{out}$—preliminary determined volume of the extracellular fluid in region between the electrodes;
$Z_{LF}$—preliminary determined low-frequency LF impedance;

3) $\Delta W_{osm}(t_k)$ is the increment of the metabolic component determined as:

$$\Delta W_{osm}(t_k)=[W_{sum}(t_{k-1})-W_{sum}(t_k)]-K_a[W_{out}(t_{k-1})-W_{out}(t_k)],$$

where: $W_{sum}(t_{k-1})$—volume of fluid in the tissues of the human body region between the electrodes measured at time $t_{k-1}$;
$W_{out}(t_{k-1})$—volume of extracellular fluid in the tissues of the human body region between the electrodes measured at time $t_{k-1}$;
$K_a$ is a factor dependent on a human hematocrit volume selected from a range from 1.2 to 2.1;

4) $\Delta G(t_k)$ is the increment of the concentration of the blood glucose determined as:

$$\Delta G(t_k)=\Delta W_{osm}(t_k) \cdot K_E \cdot K_{PR}/K_g,$$

where: $K_g$ is a normalizing factor ranging from 0.005 $l^2$millimole$^{-1}$ to 0.006 $l^2$millimole$^{-1}$;
$K_E$ is a factor selected from a range of 0.23 to 0.4 before a meal intake, and selected from a range of 0.6 to 1.0 after the meal;
$K_{PR}$ is a factor corresponding to measuring the concentration of the glucose in blood from 20 min to 45 min after the meal intake and wherein:
$K_{PR}=1$, if $\Delta W_{osm}(t_k)$ is more than 0;
$K_{PR}=-1$, if $\Delta W_{osm}(t_k)$ is less than 0.

BRIEF DESCRIPTION OF THE DRAWINGS

The invention is illustrated with the following graphic drawings.

FIGS. 1a, 2a and 3a show the graphs of variation of glucose concentration determined through the use of different methods, including the method of the present invention, while FIGS. 1b, 2b and 3b show graphs of measured values of impedance and temperature.

DETAILED DESCRIPTION OF THE PREFERRED EMBODIMENTS

Figure 1A:
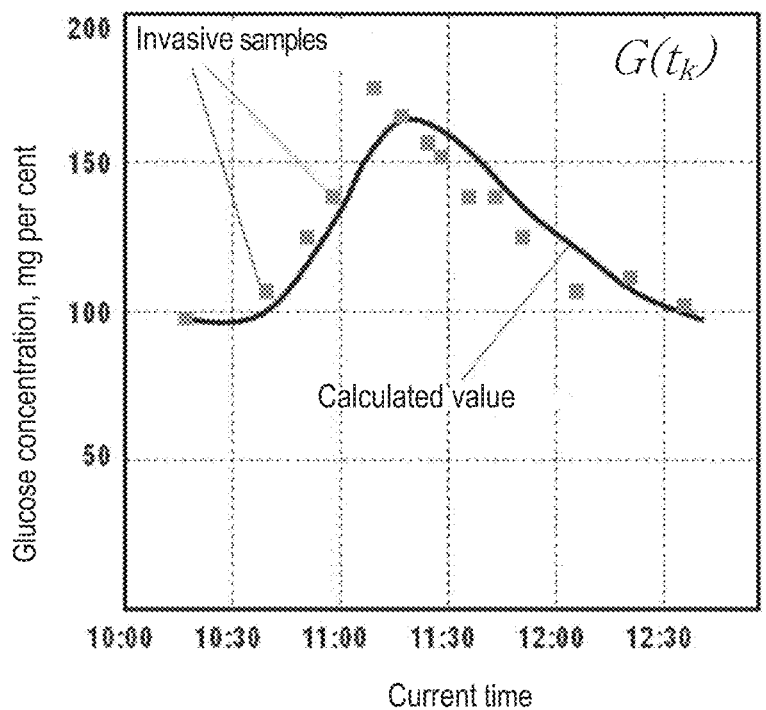
FIG. 1A is a graph showing variation of shows the results of determining glucose concentration in the blood for the first volunteer.

The method is implemented in the following way.

Two electrodes are secured on a human body region apart from one another—at distance L. It is preferable to secure electrodes on peripheral body regions—e.g. on an arm, specifically, on forearm or finger. The best result will be obtained in the case of using annular electrodes embracing forearm or a finger Since the method according to the invention claimed herein is based on calculating the values of the increment of glucose concentration in human blood followed by summing up the calculated values, prior to taking measurements of impedance, blood glucose concentration should be measured (using any other method—invasive or non-invasive one), and the value of thus measured impedance is taken as the initial one.

Impedance of a human body region is measured between electrodes at two frequencies: high frequency HF and low frequency LF. High frequency HF is chosen from the range from 200 kHz to 2 MHz; low frequency LF is chosen from the range from 20 kHz to 80 kHz. Electrical impedance of components of electrical impedance of body region tissues can be measured using one of the known methods,—specifically, by radiating high-frequency oscillations and subsequent measuring the impedance by means of capacitive sensors. Impedance of a human body region is measured at time intervals chosen from the range from 1 sec to 10 min.

A moment of food intake (characterizing glucose supply into the human body from the outside) is recorded in the course of measurements. This is done to derive the increment of metabolic component of the volume of extracellular fluid related to glucose, taking into account the time that have elapsed since the recorded moment of food intake beginning.

Based on the initial glucose concentration volume in human blood, current successive measurements of impedance of a human body region at high and low frequencies, and taking into account the time moment of food intake, glucose concentration in human blood is derived as follows.

1. The volume of fluid contained in a human body region between the electrodes $W_{sum}(t_k)$ is derived based on impedance value for human body region measured at high frequency HF at point in time $t_k$–$Z_{HF}(t_k)$, taking into account distance L between the electrodes, as follows:

$$W_{sum}(t_k) = A \cdot L^2 / Z_{HF}(t_k),$$

where: A—calibration factor, calculated from the formula:

$$A = V_{sum} \cdot Z_{HF}/L^2.$$

Here, $V_{sum}$—value (obtained in advance) of the volume of fluid contained in the tissues of human body region between the electrodes. This value can be, for instance, calculated using anatomical relationships of the human body region chosen for impedance measuring. Also, the value of impedance of a human body region measured at high frequency $Z_{HF}$ (and obtained in advance prior to the beginning of measurements intended for determining glucose concentration in human blood according to the invention claimed herein) is used for deriving calibration factor A.

2. The volume of extracellular fluid contained in the tissues of a human body region between the electrodes $W_{out}(t_k)$ is derived based on impedance value for human body region measured at low frequency LF at point in time $t_k$–$Z_{LF}(t_k)$, taking into account distance L between the electrodes, as follows:

$$W_{out}(t_k) = B \cdot L^2 / Z_{LF}(t_k),$$

where: B—calibration factor, calculated from the formula:

$$B = V_{out} \cdot Z_{LF}/L^2.$$

Here, $V_{out}$—value (obtained in advance) of the volume of extracellular fluid contained in the human body region between the electrodes. This value can be, for instance, calculated using anatomical relationships of the human body region chosen for impedance measuring. Also, the value of impedance of a human body region measured at low frequency $Z_{LF}$ is used for determining the calibration factor B. This impedance value is determined in advance prior to measurements of glucose concentration in human blood according to the present invention.

3. Then obtained value of volume of fluid contained in the tissues of the human body region between electrodes, and volume of extracellular fluid contained in the tissues of the human body region between electrodes, are used for calculating the increment of metabolic component of the extracellular fluid volume $\Delta W_{osm}(t_k)$. The values of fluid volumes obtained for measurements of impedance at point in time $t_k$ and for the previous measurement at point in time $t_{k-1}$ are used for this calculation. The increment of metabolic component of extracellular fluid volume is calculated from the formula:

$$\Delta W_{osm}(t_k) = [W_{sum}(t_{k-1}) - W_{sum}(t_k)] - K_a[W_{out}(t_{k-1}) - W_{out}(t_k)],$$

where: $W_{sum}(t_k)$—volume of fluid contained in the tissues of the human body region between the electrodes, for the current measurement taken at point in time $t_k$;

$W_{sum}(t_{k-1})$—volume of fluid contained in the tissues of the human body region between the electrodes, for the previous measurement taken at point in time $t_{k-1}$;

$W_{out}(t_k)$—volume of extracellular fluid contained in the tissues of the human body region between the electrodes, for the current measurement taken at point in time $t_k$;

$W_{out}(t_{k-1})$—volume of extracellular fluid contained in the tissues of the human body region between the electrodes, for the previous measurement taken at point in time $t_{k-1}$;

$K_a$—factor dependent on the value of human hematocrit (this factor is chosen from the range from 1.2 to 2.1).

4. The value of the increment of glucose concentration in human blood is determined based on the obtained value of $\Delta W_{osm}(t_k)$ taking into account the moment of food intake:

$$\Delta G(t_k) = \Delta W_{osm}(t_k) \cdot K_E \cdot K_{PR}/K_g,$$

where: $K_g$—the normalizing factor chosen from the range from 0.005 $l^2$millimole$^1$ to 0.006 $l^2$millimole$^{-1}$.

$K_E$—factor dependent on food intake; when determining glucose concentration in human blood prior to food intake, $K_E$ value is chosen from the range from 0.23 to 0.4, and when determining glucose concentration in human blood after food intake, $K_E$ value is chosen from the range from 0.6 to 1.0;

$K_{PR}$—factor used for determining glucose concentration in human blood in the time period from 20 to 45 minutes after food intake, with this factor taking the value either 1 or −1 depending on the sign of the said increment of metabolic component of the extracellular fluid volume according to the following rule:

$K_{PR}=1$, if the said increment of metabolic component of the extracellular fluid volume $\Delta W_{osm}(t_k)$ is greater than 0, $K_{PR}=-1$, if the said increment of metabolic component of the extracellular fluid volume $\Delta W_{osm}(t_k)$ is less than 0.

5. The final value of glucose concentration in human blood by point in time $t_k$ is derived as follows:

$$G(t_k) = G_0 + \sum_{i=1}^{k} \Delta G(t_i),$$

where: $G_0$—initial value of glucose concentration in human blood;

$\Delta G(t_i)$—values of all increments of glucose concentration in human blood obtained from the beginning of measurements till point in time $t_k$, where $i=\{1,k\}$.

Thus, knowing the initial value of glucose concentration in human blood $G_0$ and periodically taking measurements of impedance of the human body region at high and low frequencies—$Z_{HF}(t_k)$ and $Z_{LF}(t_k)$, one can derive the current value of glucose concentration in human blood. The present invention can be embodied as quite simple measuring device capable of calculating of the above-indicated parameters characterizing changes in volumes of water spaces in human tissues, and finally, the current value of glucose concentration in human blood, including the option of taking into account the individual physiological features of human being and moments of food intake.

EXAMPLES

Example 1. Processing of Measurement Data for Healthy Volunteer #1

Figure 1B:
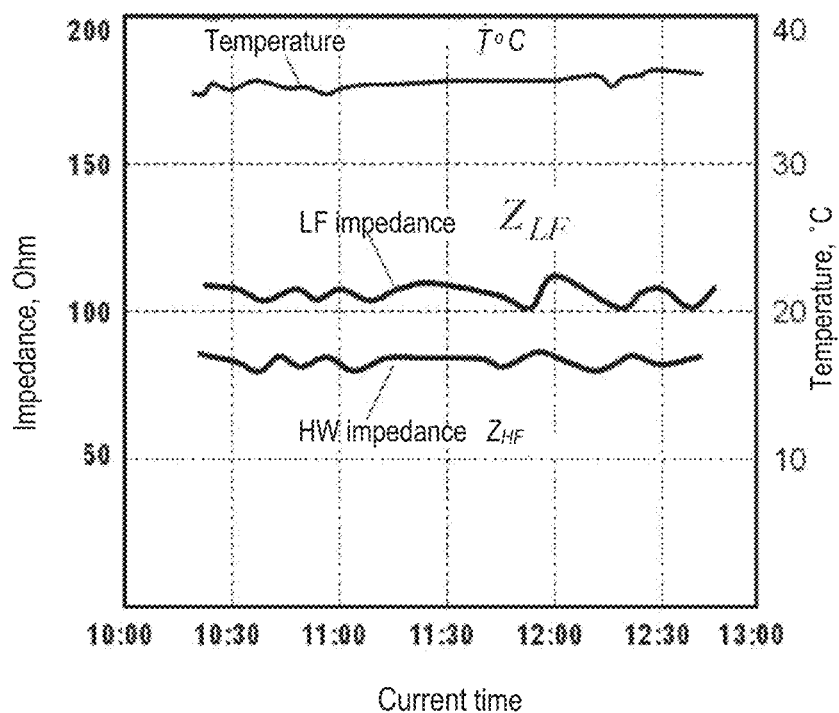
FIG. 1B is a graph showing measured values of impedance and temperature for the first volunteer.

A 38-year-old healthy male, took a meal (food load) of 300 g of sweet beverage (Pepsi Cola). FIG. 1b shows the graphs of impedance value variation $Z_{HF}$ and $Z_{LF}$ and temperature T° C. recorded by the sensor located on the forearm, while FIG. 1a shows the graph of variation of glucose concentration in the blood of Volunteer #1. Dots indicate values of blood sample taken during the measurements (Roche Accu-Chek Active glucometer was used). The mean error for the measurement interval of 150 minutes was equal to 6.8%.

Example 2. Processing of Measurement Data for Healthy Volunteer #2

Figure 2A:
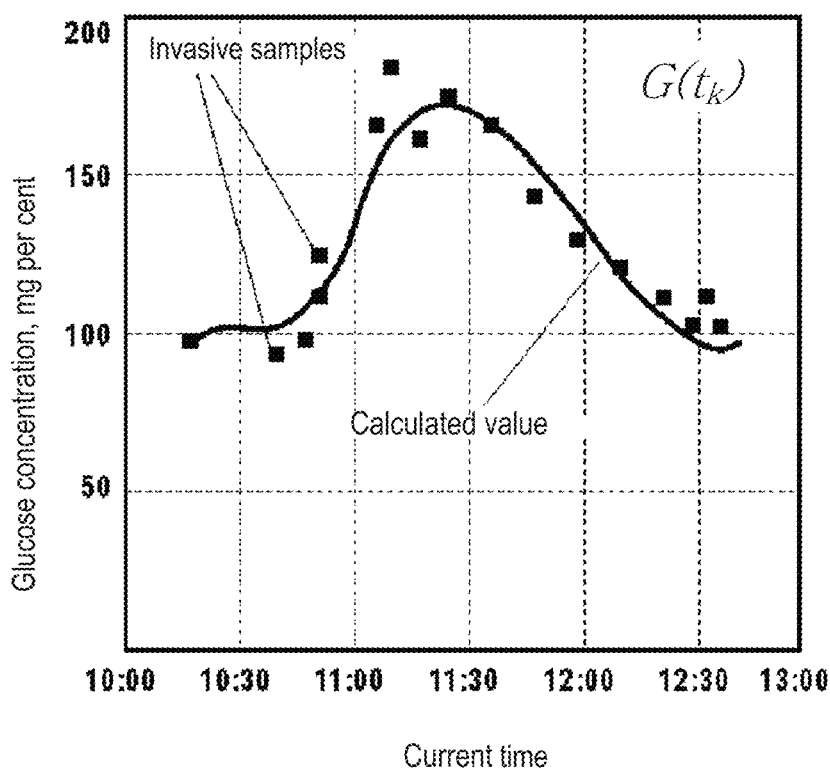
FIG. 2A is a graph showing variation of shows the results of determining glucose concentration in the blood for the second volunteer.
Figure 2B:
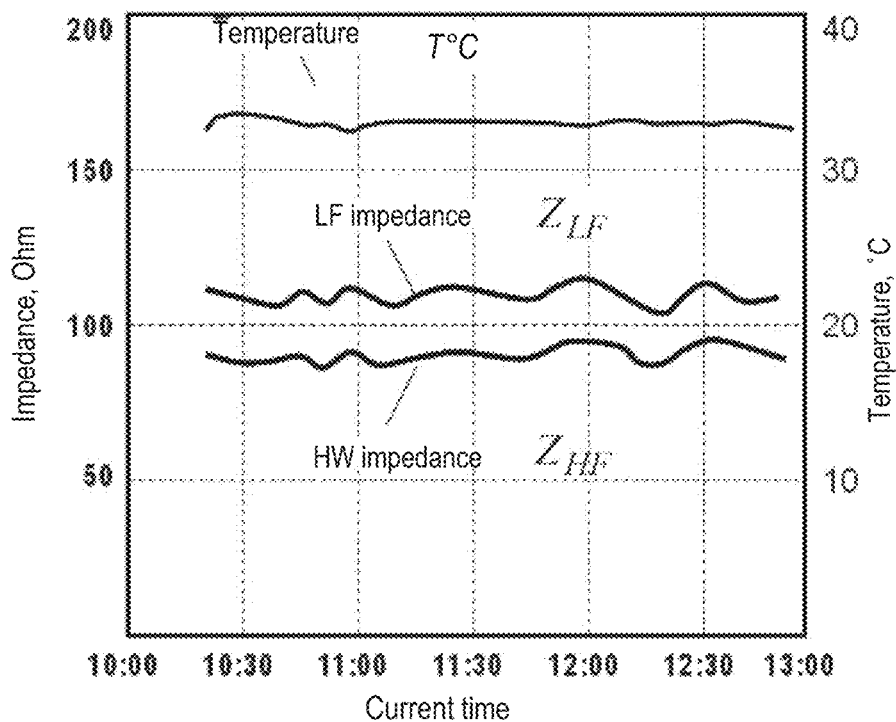
FIG. 2B is a graph showing measured values of impedance and temperature for the second volunteer.

A 45-year-old healthy male, took a meal (food load) of two 200 g glasses of sweet beverage (Pepsi Cola). FIG. 2b shows the graphs of impedance value variation $Z_{HF}$ and $Z_{LF}$ and temperature T° C. recorded by the sensor located on the forearm, while FIG. 2a shows the graph of variation of glucose concentration in the blood of Volunteer #2. Dots indicate values of blood sample taken during the measurements (Roche Accu-Chek Active glucometer was used). The mean error for the measurement interval of 140 minutes was equal to 7.2%.

Example 3. Processing of Measurement Data for Healthy Volunteer #3

Figure 3A:
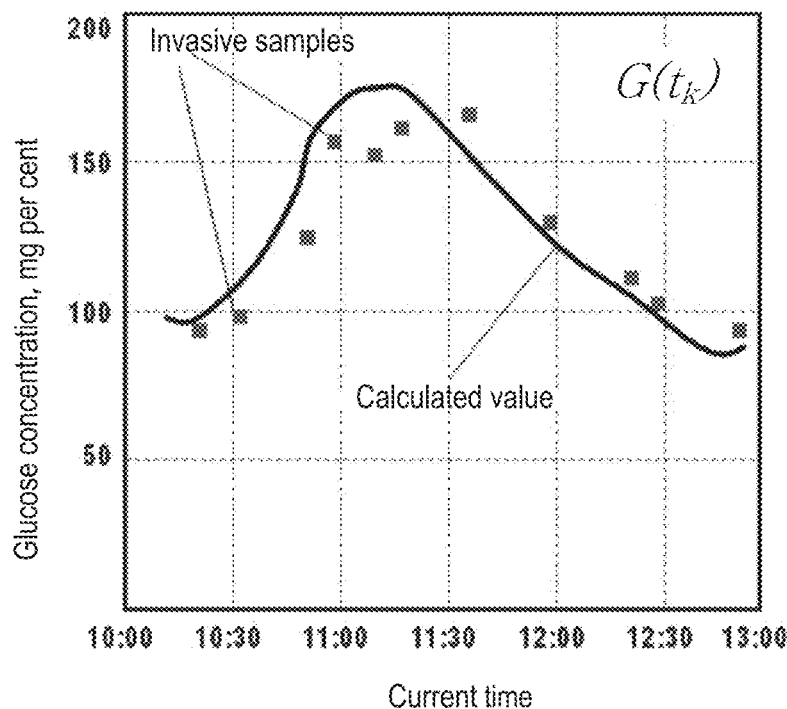
FIG. 3A is a graph showing variation of shows the results of determining glucose concentration in the blood for the third volunteer.
Figure 3B:
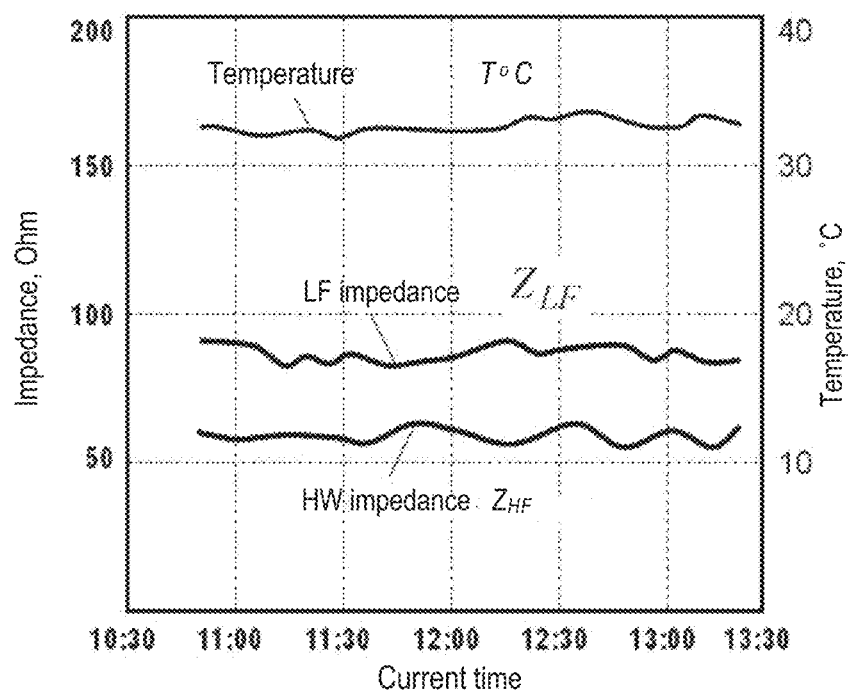
FIG. 3B is a graph showing measured values of impedance and temperature for the third volunteer.

A 42-year-old healthy male, took a combined meal (food load) of 200 g of sweet beverage (Pepsi Cola) and banana. FIG. 3b shows the graphs of impedance value variation $Z_{HF}$ and $Z_{LF}$ and temperature T° C. recorded by the sensor located on the forearm, while FIG. 3a shows the graph of variation of glucose concentration in the blood of Volunteer #3. Dots indicate values of blood sample taken during the measurements (Roche Accu-Chek Active glucometer was used). The mean error for the measurement interval of 150 minutes was equal to 9.5%.

The conducted tests showed that the method claimed herein is characterized by lesser error when determining the value of glucose concentration in human blood as compared to the known non-invasive methods.

What is claimed is:

1. A method of non-invasively measuring a concentration of glucose in blood of a human body, the method comprising:

recording a value of initial concentration of the glucose in the body;

selectively attaching a first electrode and a second electrode to spaced apart regions of the body;

measuring with pre-defined periodicity a first impedance HF of the body between the electrodes at a first frequency to determine a first volume of a fluid in the body between the electrodes, and first incremental changes of the first volume; and measuring with the pre-defined periodicity a second impedance LF of the body between the electrodes at a second frequency lower than the first frequency, to determine a second volume of an extracellular fluid in the body between the electrodes, and second incremental changes of the second volume;

using a measuring device to determine a difference between the first and second incremental changes within each time interval and to determine an increment of the concentration of the glucose by normalizing the difference to a value of the second volume; and measuring the concentration of glucose by summing the increment of the concentration of the glucose determined during performance of previous steps with the value of the initial concentration of the glucose in the body.

2. The method according to claim 1, wherein the first frequency is 200 kHz to 2 MHz and the second frequency is 20 kHz to 80 kHz.

3. The method according to claim 1, wherein the spaced apart regions are located on limbs of the body.

4. The method according to claim 3, further comprising: determining the first and second incremental changes using pre-determined algorithms.

5. The method according to claim 1, further comprising: measuring the impedance with periodicity from 1 sec to 10 min.

* * * * *